US010792125B2

(12) United States Patent
Beck et al.

(10) Patent No.: US 10,792,125 B2
(45) Date of Patent: Oct. 6, 2020

(54) SURGICAL RETAINING ARM THAT CAN BE AUTOMATICALLY RETIGHTENED

(71) Applicant: Aesculap AG, Tuttlingen (DE)

(72) Inventors: Thomas Beck, Durchhausen (DE); Dominik Seyfried, Königsfeld (DE); Robert Vogtherr, Tuttlingen (DE)

(73) Assignee: AESCULAP AG, Tuttlingen (DE)

( * ) Notice: Subject to any disclaimer, the term of this patent is extended or adjusted under 35 U.S.C. 154(b) by 95 days.

(21) Appl. No.: 16/097,889

(22) PCT Filed: May 3, 2017

(86) PCT No.: PCT/EP2017/060554
§ 371 (c)(1),
(2) Date: Oct. 31, 2018

(87) PCT Pub. No.: WO2017/191197
PCT Pub. Date: Nov. 9, 2017

(65) Prior Publication Data
US 2019/0142545 A1 May 16, 2019

(30) Foreign Application Priority Data
May 4, 2016 (DE) .................. 10 2016 108 371

(51) Int. Cl.
A61B 90/57 (2016.01)
A61B 90/50 (2016.01)
A61B 17/02 (2006.01)

(52) U.S. Cl.
CPC .............. A61B 90/57 (2016.02); A61B 17/02 (2013.01); A61B 17/0206 (2013.01);
(Continued)

(58) Field of Classification Search
CPC . A61B 17/0206; A61B 17/0218; A61B 90/57; A61B 2090/508
See application file for complete search history.

(56) References Cited

U.S. PATENT DOCUMENTS 6,464,629 B1 10/2002 Boone et al.
6,506,149 B2 1/2003 Peng et al.
(Continued)

FOREIGN PATENT DOCUMENTS

DE 29511900 U1 9/1995
DE 102010035407 A1 3/2012
(Continued)

OTHER PUBLICATIONS

WO 2014/140316 Machine translation. (Year: 2014).*
(Continued)

Primary Examiner — Carrie R Dorna

(57) ABSTRACT

A surgical device for stabilizing tissue or positioning organs, or for positioning and holding surgical instruments and devices during a surgical intervention, includes a main body and a flexible arm. The flexible arm can be fastened to the main body, which can be brought into different positions and/or locations and which can be locked in a desired positioning by a tightening mechanism. The tightening mechanism can be tightened and/or released self-actingly and/or by an energy source. In a locked state of the flexible arm, the tightening mechanism has a retightening reserve, and the flexible arm can be automatically retightened in order to maintain its locked state, in particular by an introduction of energy from the energy source or self-actingly, by utilization of the retightening reserve. A retightening mechanism for use in the surgical device automatically retightens a flexible arm when in a locked state to maintain its locked state.

10 Claims, 5 Drawing Sheets

(52) U.S. Cl.
    CPC ........ *A61B 90/50* (2016.02); *A61B 2090/508* (2016.02); *A61B 2090/571* (2016.02)

(56) References Cited

U.S. PATENT DOCUMENTS

| | | |
|---|---|---|
| 6,866,628 B2 | 3/2005 | Goodman et al. |
| 7,736,307 B2 | 6/2010 | Hu et al. |
| 10,098,623 B2 | 10/2018 | Vogtherr et al. |
| 2006/0004250 A1 | 1/2006 | Parihar et al. |
| 2009/0247819 A1 | 10/2009 | Wilson et al. |
| 2015/0012021 A1 | 1/2015 | Mihara |
| 2016/0030031 A1 | 2/2016 | Vogtherr et al. |
| 2017/0245844 A1 | 8/2017 | Vogtherr et al. |

FOREIGN PATENT DOCUMENTS

| | | |
|---|---|---|
| DE | 102013102628 A1 | 10/2014 |
| DE | 102014104179 A1 | 10/2015 |
| WO | 2014140316 A2 | 9/2014 |

OTHER PUBLICATIONS

International Search Report and Written Opinion for International Application No. PCT/EP2017/060554, dated Jul. 10, 2017—7 pages.
German Search Report for Application No. 10 2016 108 371.2, with English translation, dated Mar. 8, 2017—18 pages.

\* cited by examiner

SURGICAL RETAINING ARM THAT CAN BE AUTOMATICALLY RETIGHTENED

RELATED APPLICATIONS

This application is the United States national phase entry of International Application No. PCT/EP2017/060554, filed May 3, 2017, which is related to and claims the benefit of priority of German Application No. 10 2016 108 371.2, filed May 4, 2016. The contents of International Application No. PCT/EP2017/060554 and German Application No. 10 2016 108 371.2 are incorporated by reference herein in their entireties.

FIELD

The invention relates to a surgical device for stabilizing tissue or for positioning organs or for positioning and holding surgical instruments and devices during a surgical intervention, comprising a main body and a flexible arm, in particular an articulated arm, which in particular is or can be fastened to the main body, which can be brought into different positions and/or locations and which can be locked in a desired positioning by means of a tightening mechanism, the tightening mechanism being tightened and/or released self-actingly and/or by means of an energy source. In addition, the invention relates to a retightening mechanism for a surgical working arm.

BACKGROUND

Many surgical procedures today use power-operated, movable retaining arms that can hold, move or control specific surgical devices or instruments. For example, such movable retaining arms can be transferred from a locked state to a moving state by means of compressed air and clamped or locked by means of spring force, while the compressed air can be controlled by means of an electrical circuit and electrical actuating elements. Such a power-operated, movable retaining arm is known from DE 10 2013 102 628 A1, for example.

The retaining arm according to DE 10 2013 102 628 A1 consists of a plurality of individually movable, hemispherical links and a cable passed through the center of these links, the distal end of which is attached to the last movable link of the arm and the proximal end of which can be moved in the longitudinal direction by a tightening mechanism. The links are bounded at the proximal end of the arm by a stationary component, so that the links of the arm are pressed against each other when the cable is pulled back in the longitudinal direction, the arm being locked thereby. If the cable is moved toward the distal end, however, there is again play between the links so that they become free of each other and the entire arm can be moved.

The articulated arm according to DE 10 2013 102 628 A1, like many other generic retaining arms, is intended for single use only, as it cannot be conditioned or sterilized due to its design and geometry. It therefore consists largely of plastic materials and as part of a two-piece structure is attached to a main body. The individual links of the movable arm are subject to a certain deformation and compression during the tensile force application necessary for locking the arm, whereby the entire articulated arm becomes a little shorter in the tightened condition. On the other hand, the inside force-transmitting cable expands and becomes longer under load. As a result, the retaining arm yields, becomes loose and thus cannot maintain its locked state. Since the adjustment mechanism of DE 10 2013 102 628 A1, which is moved by spring force, is driven against a mechanical stop, such compression of the articulated arm segments and elongation of the cable cannot be compensated.

From document DE 29 511 900 U1, a double compressed air piston for moving a mechanical system tightened by spring force is known, whereas this does not represent a comparable retaining arm, with which many articulated arm segments are tightened by means of a traction cable, from which the problematic changes in lengths result during operation. As a result, DE 29 511 900 U1 also does not provide for retightening to compensate for expansion and compression.

In the state of the art, on the other hand, retaining arms are known which work for tightening or retightening by means of a manual tightening device such as a screw mechanism, for instance. These tightening devices adjust the tensile force and the associated length compensation required to generate the tensile force once at the beginning of the application. Such manual tightening devices are known from the documents U.S. Pat. No. 6,464,629 B1, U.S. Pat. No. 6,866,628 B2, U.S. Pat. No. 7,736,307 B2 and U.S. Pat. No. 6,506,149 B2, for example.

In these documents, the tensile force for tightening the traction cable in the arm and thus to lock the articulated arm is applied by means of a screw or another actuating element to be manually operated by a user, so that the tensile force is initially fixed at a certain point in this setting. However, even with such manual tightening devices, the tightening force decreases to a certain extent over a certain period of time due to elastic and/or plastic changes in the length of the articulated arm or due to the elongation of the traction cable, and the articulated arm is no longer as firmly locked as it was at the beginning. During the application period of such an articulated arm, the screw must therefore be actuated after a certain time or after certain time intervals and the atm must therefore be manually retightened. According to these documents, the user then has the option of retightening the screw and retightening the arm manually.

The state of the art thus has the disadvantage that a retightening of the articulated atm is either not planned or has to be carried out manually by a user in a laborious manner. In the solutions known so far, there is therefore no retightening of the articulated arm without the user's intervention.

SUMMARY

It is therefore the object of the present invention to avoid or at least mitigate the disadvantages arising from the prior art. In particular, an initially set or technically determined tightening force should be maintained without the user's intervention and a locking of a surgical articulated arm should thus be guaranteed over a long period of time without the user's intervention.

The invention first relates to a surgical device for stabilizing tissue or for positioning organs or for positioning and holding surgical instruments and devices during a surgical intervention, comprising a main body and a flexible arm, in particular an articulated arm, which in particular is or can be fastened to the main body, which can be brought into different positions and/or locations and which can be locked in a desired positioning by means of a tightening/tensioning mechanism, wherein a tightening/tensioning and/or releasing/loosening takes place self-actingly and/or by means of an energy source, and wherein, in a locked state of the flexible arm, the tightening mechanism has a retightening/ retensioning reserve, in particular a retightening reserve travel, and the flexible arm can be automatically retightened in order to maintain its locked state, in particular by an introduction of energy from the energy source or self-actingly, by utilization of the retightening reserve.

According to the invention, in particular a two-piece surgical device is provided, consisting of a main body and a flexible articulated arm which is attached or can be attached thereto. The articulated arm is made of plastic material and intended for single use. The articulated arm is basically freely movable and movable in itself and can be locked or clamped or "frozen" in any position or location via a tightening mechanism, if required. The tightening mechanism can be tightened and/or released self-actingly, for example by spring force or by means of an external energy source. As external energy sources, hydraulic or pneumatic pressure sources or an electrical energy source are conceivable.

If the present system or the present surgical device is designed such that there is a retightening reserve/a retightening reserve travel/a travel reserve in an operating point or in a locked state of the flexible arm, and the flexible arm can be retightened automatically by using the retightening reserve to maintain its locked state, an initial tightening force can be maintained—without the intervention of a user—and a locking of the articulated arm can be guaranteed over a long period of time. This has the advantage that a user, in particular a doctor or surgeon, can always rely on a suitable tightening force of the tightening mechanism even after a long period of time and that the locked state is maintained without any action on his part. This is extremely advantageous in surgical interventions or operations in which the surgical device of the invention is used.

The surgical device according to the invention must be designed in such a way that the retightening reserve is given in all possible positions and locations of the flexible arm. The construction and design of main body and flexible arm must therefore be matched in such a way that the retightening reserve travel according to the invention is given in every operating position. Automatic retightening can be carried out independently, for example by means of spring force, or by introducing energy or force from the energy source.

It has proven to be particularly advantageous if the tightening of the tightening mechanism is carried out self-actingly by means of spring force and the releasing of the tightening mechanism is carried out by means of the energy source, wherein the retightening reserve is available in the form of a spring travel reserve present in the locked state of the flexible arm.

According to this exemplary embodiment, the flexible arm or articulated arm is thus tightened or locked by means of spring force, whereas the loosening of the flexible arm is carried out or achieved by means of the energy source and in particular by means of force application against the spring tension force. The normal state or basic state in this exemplary embodiment is therefore the tightened state. An actuating element allows the user to cancel the tightened or locked state by applying force against the spring force by means of the energy source. This exemplary embodiment has the particular advantage that no energy is required from the energy source in the locked state. This means that there is no energy consumption in the locked state.

If the spring for tightening the flexible arm still has a spring travel reserve in the locked state or initial operating point of the arm, any infinitesimal change in length caused by compression or expansion is automatically compensated directly or immediately or simultaneously by the spring force using the spring travel reserve. The advantage of this is that automatic retightening is easily carried out using a mechanical solution. In other words, the present system is designed in such a way that in the locked state of the flexible arm there are reserves in terms of travel and tension and thus there is no limitation of spring travel by, for example, a stop. Thus, the tightening mechanism can retighten the flexible arm automatically and simultaneously with the change in length over a long period of time and maintain the locking state even in the event of a progressive change in length due to expansion or compression. According to this exemplary embodiment, no position monitoring or control is necessary to maintain the locked state.

Another advantageous exemplary embodiment is characterized by an electric control unit which, in the locked state of the flexible arm, detects a change, in particular a reduction, in a tightening state of the tightening mechanism and controls an automatic retightening of the tightening mechanism based on the detection result, in particular by an introduction of energy from the energy source.

According to the invention, both tightening and retightening as well as the releasing of the tightening mechanism can be carried out by an introduction of energy/force or by a control of the introduction of energy/force from the energy source. In other words, tightening is achieved by introduction or application of a force in the tightening direction and releasing is achieved by introduction or application of a force against the tightening direction or in the opposite direction. The tightening and releasing of the tightening mechanism is carried out at the user's request. For example, corresponding actuating elements can be provided on the surgical device according to the invention.

In a tightening state of the tightening mechanism, a detection device, such as a force sensor, of the electric control unit continuously detects the instantaneous or current tightening state of the tightening mechanism. Based on the detection result, the electric control unit controls the introduction of energy or force from the energy source so that the tightening state can be maintained over a longer period of time without the user's intervention.

In an advantageous manner, an electric actuating motor is provided, which has a detection device, in particular a force sensor, which detects the change, in particular the reduction, in the tightening state of the tightening mechanism and which automatically retightens the flexible arm on the basis of a control by the electric control unit and based on the detection result of the detection device.

According to this, an electric actuating motor is provided in the main body as an energy source. This actuating motor is controlled by the electric control unit. In principle, the electric actuating motor can tighten or lock the flexible arm by applying force in the tightening direction and loosen the flexible arm or make it moveable by applying force against the tightening direction. This in turn can be set by the user by means of corresponding operating elements. In the locked state of the arm, the electric control unit, which may be provided so as to be integrated in the electric actuating motor, for example, detects a change in the tightening state of the tightening mechanism via a force sensor, for instance. The introduction of energy is controlled or regulated by the electric actuating motor based on the detection result.

In this preferred exemplary embodiment, the tensile force or tightening force is thus generated by means of an electric (actuating) motor equipped with a force sensor. If a change in tightening force occurs due to changes in the length of the arm, the force initially set is generated again by means of a control. The actuating motor thus maintains the required tightening force.

According to the invention, the retightening reserve may be formed or released by a stop which can be linearly displaced in the main body in particular by means of the energy source.

Such formation of the retightening reserve can be of this sort in which the tightening mechanism is tightened by spring force and the spring travel is initially limited by a stop in the initial operating point or locked state of the articulated arm. During operation of the surgical device of the invention, in particular during the tightened state, the tightening state is monitored by the detection device of the electric control unit. If there is no longer sufficient tension according to a detection result, the stop can be shifted linearly in the tightening direction by means of the energy source. Retightening then occurs in conjunction with the displacement of the stop via the available or thus released spring travel reserve.

On the other hand, this formation of the retightening reserve may also be such that tightening of the tightening mechanism is carried out by a pneumatic, hydraulic or electromotive introduction of energy and a travel of an adjusting mechanism used, for example, is limited by the stop. If it is now detected that retightening is necessary, the stop can be shifted linearly and thus the desired or suitable tightening state can be restored by a further introduction of energy. A time-controlled or time-dependent retightening is also conceivable according to the invention.

In an advantageous manner, the tightening mechanism has a traction cable which is passed through a plurality of mutually movable articulated segments of the flexible arm and via which the articulated segments can be frictionally clamped against each other, and an actuating mechanism which can be actuated self-actingly and/or by means of the energy source for actuating the traction cable.

According to the invention, the flexible arm of the surgical device is thus designed such that one distal end is provided with a holding element which is adjoined by a plurality of hemispherical articulated segments towards the proximal end of the flexible arm, with a cable being passed through the middle of said segments. The cable can be attached distally, for example, to the retaining element or the last movable articulated segment of the arm. At the proximal end of the arm, on the one hand, the articulated segments are bounded by a stationary component, and on the other hand, the cable is attached to an actuating mechanism which is arranged to be displaceable in the main body. If the actuating mechanism is now moved together with the proximal end of the cable in the proximal direction, the plurality of articulated segments are tightened or clamped between the holding element and the last movable, distal articulated segment of the arm and the stationary component. The arm is then in its locked, immobile state.

In this condition, a retightening reserve or a retightening reserve travel must exist in accordance with the invention. The setting mechanism must therefore not have already moved against a stop in the initial tightened or locked state or in the operating point. This makes it clear that the individual components of the surgical device according to the invention must be precisely matched to one another. In particular, a minimum tightening reserve travel must be provided in all possible locations and positions of the flexible arm. According to the invention, the aim is to be able to compensate for changes in length of up to 5%, preferably up to 10%, which are caused by compression of the articulated segments and elongation of the cable. It is therefore a central aspect of the present invention to design the cable, the individual articulated segments, the tightening force as well as the tightening mechanism and the main body in such a way that this minimum retightening reserve travel can be guaranteed in every case.

It is therefore useful if the actuating mechanism is linearly movable within the main body for tightening and/or releasing the tightening mechanism and the retightening reserve is formed by a linear displacement ability, which is still present in the locked state of the flexible arm, of the actuating mechanism in the tightening direction on a retightening reserve travel. It is also useful if the actuating mechanism can be actuated hydraulically, pneumatically or by an electric motor, in particular by means of the energy source controlled by the electric control unit, and the electric control unit thus controls or regulates a fluid pressure and/or an effective electrical power at the actuating mechanism.

An advantageous exemplary embodiment is characterized in that the actuating mechanism is designed in the manner of a cylinder-piston mechanism, comprising at least one, preferably two, piston chambers into which a hydraulic or pneumatic energy can be introduced for tightening and/or releasing and/or retightening the tightening mechanism, wherein the tightening mechanism is tightened and retightened preferably exclusively by at least one, preferably two, compression springs or tension springs.

In a preferred embodiment according to the invention, the actuating mechanism is designed like a cylinder-piston mechanism and has one, two or more piston chambers or actuating chambers which are arranged one behind the other in the longitudinal direction in a cylinder provided in the main body. The piston chambers, in each of which a piston is slidably mounted, can be filled with a pneumatic or hydraulic medium. The preferably two pistons are connected to a common actuating element, whereby the actuating element is in turn connected to the traction cable. The pistons apply a force to the actuating element preferably when the piston chambers are filled in the same direction at the same time. By using two pistons in particular, a larger effective piston area is achieved so that the forces acting on the actuating element are increased.

In this embodiment, two compression springs are provided for tightening or locking the flexible arm. However, tension springs are also conceivable. Tightening and retightening of the flexible arm is preferably done exclusively via the springs. The use of two springs provides increased safety, for example in the theoretically possible case of mechanical failure of one spring. On the other hand, the is preferably released exclusively by pneumatic or hydraulic actuation. By using a double piston, it is possible to apply less force or energy for releasing the arm as compared to just one piston. This makes energy savings possible. Since tightening and retightening is carried out exclusively in a mechanically simple manner by spring force, no complex control of the tightening force is required. The spring travel reserve, which is provided in the initial operating point, is, in other words, used directly by the two compression springs at every infinitesimally small change in length due to elongation of the cable or compression of the articulated segments, and automatic retightening takes place simultaneously with the change in length in a mechanically simple manner.

In this preferred embodiment, a tensile force for tightening the retaining arm is generated by means of spring force in that a piston mechanism connected to the traction cable is moved by a compression spring in the longitudinal direction opposite to the articulated arm. If this system is designed in such a way that, after initial length compensation, the piston mechanism moved by the compression spring does not hit a mechanical stop, but still has travel or tension reserves, the retightening mechanism according to the invention can automatically retighten the articulated arm over a long period of time even in the event of a further change in length, so that the locking of the arm is maintained. According to the invention, the piston mechanism may consist of one, two or more pistons, of one, two or more piston chambers and of one, two or more compression springs or tension springs. The articulated arm is loosened or released hydraulically or pneumatically.

On the other hand, it is also conceivable according to the invention that tightening and retightening of the tightening mechanism is effected in addition to the spring force by introducing the hydraulic or pneumatic energy, in particular by applying a force in the tightening direction, and the loosening of the tightening mechanism is effected exclusively by introducing the hydraulic or pneumatic energy, in particular by applying a force against the tightening direction. The spring force can therefore also be supported by hydraulic or pneumatic energy during tightening and retightening, which in turn results in increased safety.

Furthermore, the invention relates to a retightening mechanism for a surgical working arm, comprising a main body and a flexible arm, in particular an articulated arm, the flexible arm being capable of being brought into different positions and/or locations, the retightening mechanism being designed in particular for use in a surgical device as described above, and the retightening mechanism automatically retightening the flexible arm when in a locked state to maintain its locked state.

In particular, in a locked state of the flexible arm, the retightening mechanism provides a retightening reserve, in particular a retightening reserve travel, and automatically retightens the flexible arm to maintain its locked state, in particular by an introduction of energy from the energy source or self-actingly by utilization of the retightening reserve.

In other words, the invention relates to the automatic retightening of a surgical retaining arm/articulated arm. In particular, according to the invention, an initially set or technically determined tensile force or tightening force is to be maintained and a surgical articulated arm is to be locked over a long period of time without the intervention of a user. In other words, the invention preferably includes a tensile force mechanism with tightening reserve at the operating point in order to compensate for changes in length caused by elongation and compression and to maintain the tensile force or tightening force permanently and self-actingly.

BRIEF DESCRIPTION OF THE DRAWING FIGURES

The invention is explained in more detail below with the help of Figures in which.

The Figures are only schematic in nature and serve exclusively for the understanding of the invention. Identical elements are marked with the same reference symbols.

DETAILED DESCRIPTION

Figure 1:
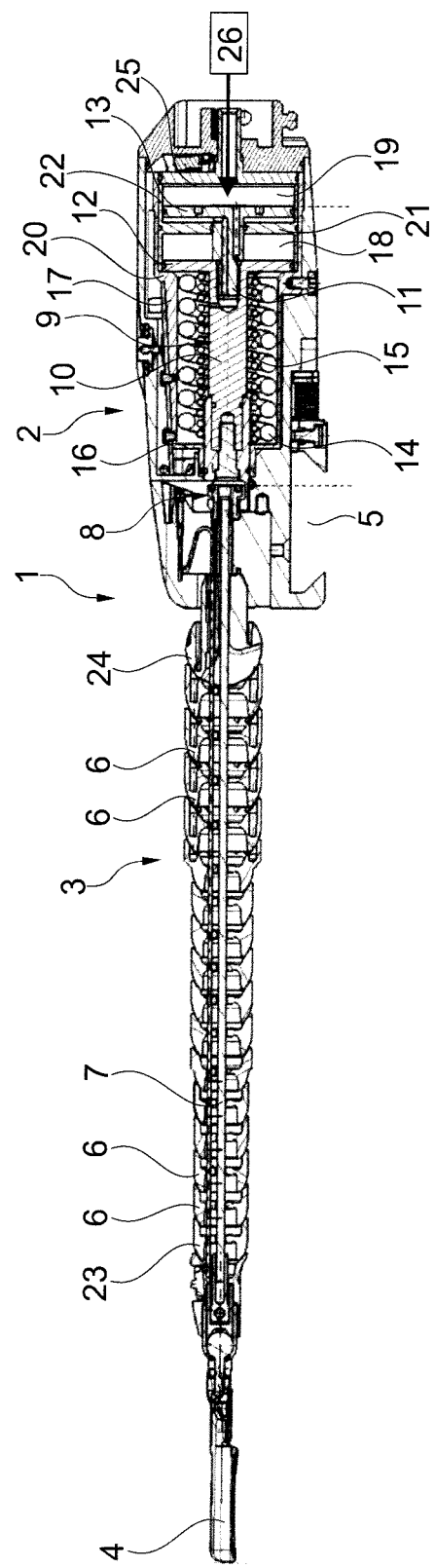
FIG. 1 is a longitudinal section view of the surgical device of the invention according to a first preferred embodiment in a movable condition of the articulated arm.
Figure 2:
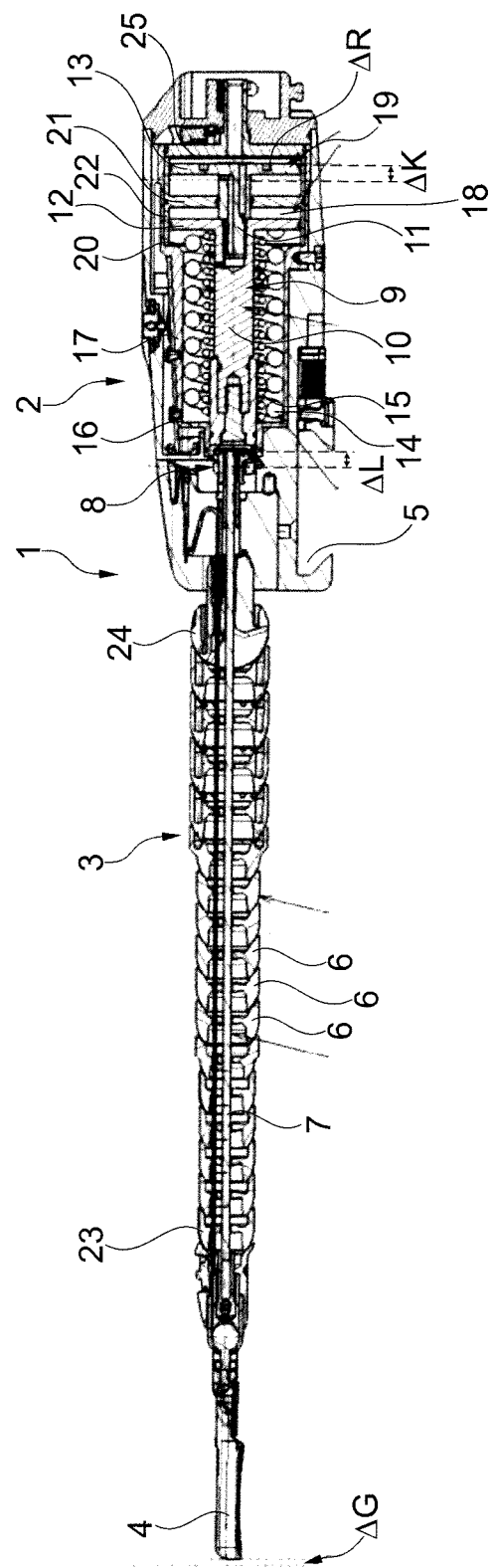
FIG. 2 is a longitudinal section view of the surgical device of the invention according to the first embodiment of FIG. 1 in a locked state of the articulated arm.

FIG. 1 and FIG. 2 illustrate a surgical device 1 according to a preferred embodiment of the present invention. The device 1 has a main body or technical block 2 to which a flexible articulated arm 3 is attached. A holding element 4 is provided at the free distal end of the articulated arm 3. The technical block 2 essentially contains the entire technical system for tightening the articulated arm 3 as well as a fixing device 5 for fixing the entire system to an external bracket that is not shown. The technical block 2 constitutes a reusable technical module and the articulated arm 3 together with the holding element 4 constitutes a working module designed for single use. The articulated arm 3 comprises a plurality of hemispherical articulated arm segments 6 and a traction cable 7 is passed through the center thereof.

FIG. 1 shows the articulated arm 3 in a freely movable state. The individual articulated arm segments 6 are thus not frictionally clamped against each other, but are movable relative to each other. This becomes particularly obvious when looking at the tightening mechanism within the technical block 2. The traction cable 7 is attached to an adapter section 8 within the technical block 2, which in turn is attached to or screwed to a piston mechanism 9. The piston mechanism 9 is designed in FIG. 1 in two parts, together with the adapter section 8 slidably arranged within the technical block 2 and consists of a distal first piston rod section 10 and a proximal second piston rod section 11, the second piston rod section 11 being fastened to or screwed to the first piston rod section 10.

Disc-shaped pistons 12, 13 are provided at the proximal ends of the first piston rod section 10 and the second piston rod section 11. Concentric to the first piston rod section 10 or around it, two compression springs 14, 15 are provided which are supported in the proximal direction by the first piston 12. In the distal direction, the compression springs 14, 15 are supported by a partition wall 16 formed on an inner part of the main body 17, which in turn is a stationary, immovable part of the main body or technical block 2.

In the respective proximal direction from the pistons 12, 13, piston chambers 18, 19 are provided within the technical block 2, which in FIG. 1 are pressurized pneumatically or hydraulically by means of an energy source 26 in such a way that the first piston 12 has moved to a stop 20 formed on the inner part of the main body 17 against the spring force of the compression springs 14, 15. In the piston chambers 18, 19 in FIG. 1, a sufficiently high force acts on the pistons 12, 13 in the distal direction so that the spring force of the compression springs 14, 15 is overcome and the piston mechanism 9 is moved to the stop 20.

Between the first piston space 18 and the second piston 13, a disc-shaped intermediate wall 21 is installed which is sealed off from the piston mechanism 9. The intermediate wall 21 is part of an inner part 22 of the guide on which the piston mechanism 9 and in particular the pistons 12, 13 are guided.

FIG. 2 shows the articulated arm 3 in a tightened or locked state. The articulated arm segments 6 are frictionally tensioned against each other in FIG. 2 and clamped between a distal articulated arm end segment 23, to which the traction cable 7 is attached, and a stationary proximal end segment 24. Looking at the tightening mechanism in FIG. 2, it becomes clear that the piston chambers 18, 19 are no longer pressurized hydraulically or pneumatically, since the piston 12 has moved away from the stop 20 and the compression springs 14, 15 now provide for tightening the articulated arm segments 6. The compression springs 14, 15 thus press on the first piston 12 in such a way that the entire piston mechanism 9 is pushed away from the stationary partition wall 16 in the proximal direction. This happens automatically as soon as no hydraulic or pneumatic pressure is exerted from the piston chambers 18, 19 onto the pistons 12, 13.

FIG. 2 shows the travel ΔK of the piston mechanism 9 for tightening the articulated arm 3. The travel ΔK corresponds to the initial change in length ΔL, which is required for tightening the articulated arm 3. The change in length ΔL already includes an initial compression ΔG of the articulated arm segments 6 and an initial elongation ΔS of the traction cable 7. In the tightened state of FIG. 2 or in the operating point present in this state, the piston mechanism 8 has a retightening reserve ΔR. In other words, the piston 13 does not hit the piston chamber limitation 25 in the operating point, but a spring travel reserve ΔR is still available.

If, with increased lifetime, the tightened or locked operation of the articulated arm 3 shows a progressive compression of the articulated arm segments 6 and a progressive elongation of the traction cable 7, such change in lengths are compensated immediately or simultaneously with each infinitesimally small change in length by the piston mechanism 9 still being displaceable in the proximal direction with the help of the two compression springs 14, 15 due to the spring travel reserve ΔR still available. The entire possible travel ΔV is thus composed of the initial travel ΔK and the spring travel reserve ΔR available at that time. Consequently, ΔV=ΔK+ΔR.

Figure 3:
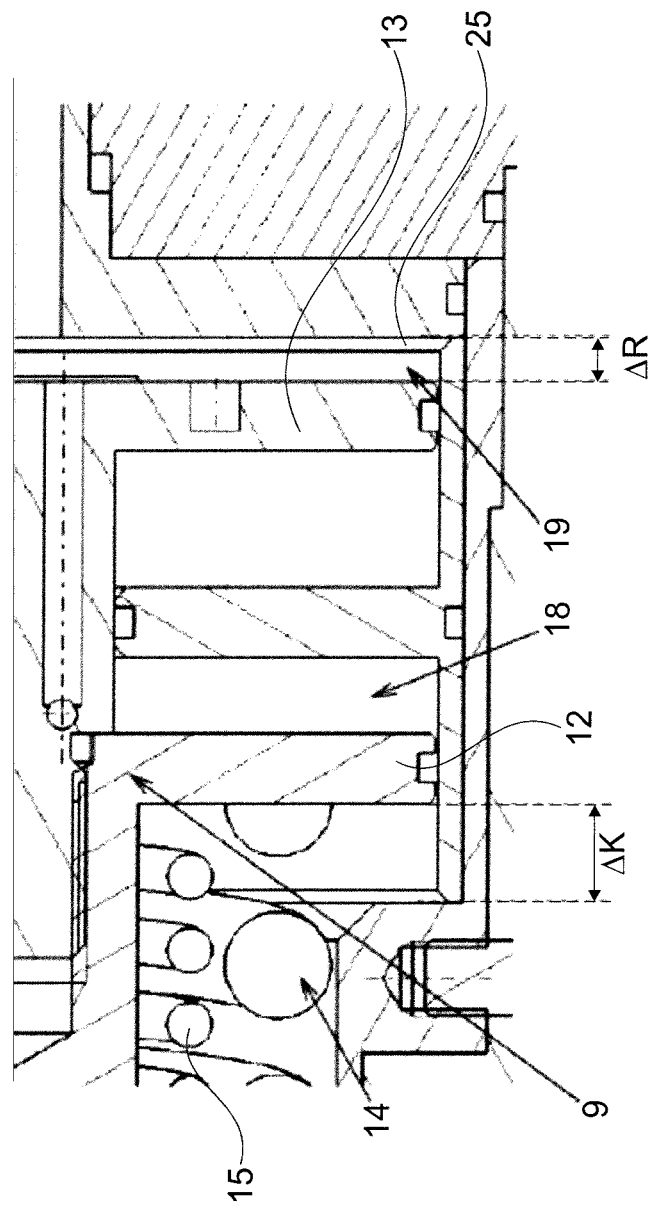
FIG. 3 is an enlarged view of the tightening mechanism of the surgical device of the invention according to the first embodiment of FIG. 1 and FIG. 2.

This is illustrated even better in FIG. 3 in particular. Here, it becomes clear once again that the piston 12 in the tightened state of the articulated arm 3 is shifted away from the stop 20 in the proximal direction by the initial travel ΔK. In this condition, in which the piston chambers 18, 19 are not pressurized hydraulically or pneumatically, there is still a retightening reserve or spring travel reserve ΔR over to the initial travel ΔK. By means of the spring travel reserve ΔR, compressions of the articulated arm segments 6 and expansions of the traction cable 7 can be compensated until the second piston 13 strikes against the piston chamber limitation 25.

The spring travel reserve ΔR is particularly selected such that the expansions and compressions occurring during operation of the articulated arm 3 can be compensated in any case. Accordingly, the spring travel reserve ΔR depends on the rigidity or strength of the traction cable 7 and articulated arm segments 6 and thus in particular on the material used in each case. Thus, the expected expansions and compressions can be determined experimentally, for example by tensile tests, for any material and the spring travel reserve ΔR can be designed accordingly.

Figure 4:
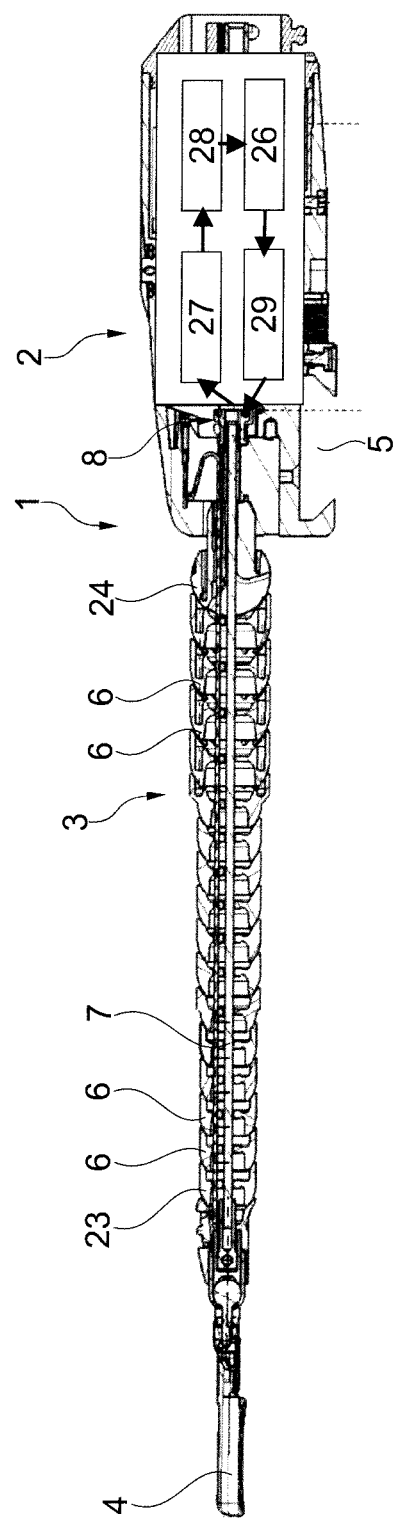
FIG. 4 is a longitudinal section view of the surgical device of the invention according to a second preferred embodiment.

FIG. 4 shows a longitudinal section view of the surgical device of the invention according to a second preferred embodiment in which both tightening and automatic retightening as well as releasing of the tightening mechanism take place by an introduction of energy/force from an energy source 26. In the second preferred embodiment, the automatic retightening mechanism is implemented within technical block 2 as follows: A detection device 27, for example a force sensor, detects a tightened state of the traction cable 7 attached to the adapter section 8 in the locked state of the articulated arm 3 and transmits the detected data to an electrical control unit 28 monitoring a change in the tightened state. The electric control unit 28 controls an energy source 26 or the introduction of energy/force from the energy source 26. The energy source 26 provides an electric actuating motor 29 with energy, which in turn actuates/retightens the traction cable. In other respects, the description relating to FIGS. 1 to 3 applies analogously to FIG. 4.

Figure 5:
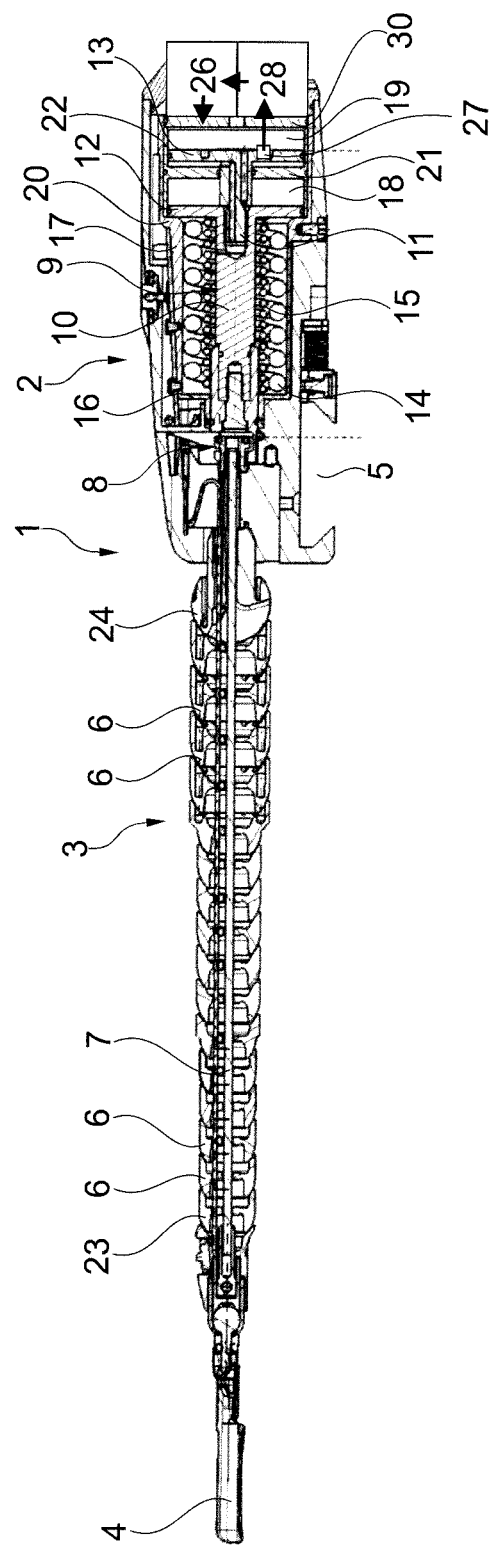
FIG. 5 is a longitudinal section view of the surgical device of the invention according to a third preferred embodiment in a movable state of the articulated arm.

FIG. 5 shows a longitudinal section view of the surgical device of the invention according to a third preferred embodiment in a movable state of the articulated arm. In FIG. 5, the piston chambers 18, 19 are pressurized pneumatically or hydraulically (see FIG. 1) in such a way that the first piston 12 has hit a stop 20 formed on the inner part 17 of the main body against the spring force of the compression springs 14, 15. If the hydraulic or pneumatic energy is removed/switched off in the state shown in FIG. 5, the second piston 13 moves against a linearly movable stop 30. The flexible arm 3 is then in a tightened/locked state. The automatic tightening mechanism is implemented in the third embodiment as follows: A detection device 27 provided on the second piston 13, for example a force sensor, detects a tightening condition which is monitored by an electric control unit 28. If there is no longer sufficient tensioning, the linearly movable stop 30 can be shifted linearly in the tightening direction by means of an energy source 26. When the linearly movable stop 30 is moved, a spring travel reserve ΔR is released. In other respects, the description to FIGS. 1 to 3 applies analogously to FIG. 5.

The invention claimed is:

1. A surgical device for stabilizing tissue or for positioning organs or for positioning and holding surgical instruments and devices during a surgical intervention, comprising a main body and a flexible arm, which can be brought into different positions or locations and which can be locked in a desired positioning by a tightening mechanism, the tightening mechanism being tightened self-actingly by spring force and being released by an energy source, wherein, in a locked state of the flexible arm, the tightening mechanism has a retightening reserve, and the flexible arm can be automatically retightened in order to maintain a locked state using the retightening reserve, the retightening reserve being formed by a spring travel reserve available in the locked state of the flexible arm such that, in the locked state of the flexible arm, a travel reserve and a tightening reserve are available, and there is no limitation of spring travel by a stop.

2. The surgical device according to claim 1, wherein the tightening mechanism comprises a traction cable which is passed through a plurality of mutually movable articulated segments of the flexible arm and via which the articulated segments can be frictionally clamped against each other, and a cylinder-piston actuating mechanism which can be actuated self-actingly by spring force or by the energy source for actuating the traction cable, wherein the cylinder-piston actuating mechanism has not already moved against the stop in the initially tightened, locked state of the flexible arm.

3. The surgical device according to claim 2, wherein the cylinder-piston actuating mechanism is linearly movable within the main body for tightening or releasing the tightening mechanism, and the retightening reserve is formed by a linear displaceability, which is still present in the locked state of the flexible arm, of the actuating mechanism in the tightening direction on a retightening reserve travel.

4. The surgical device according to claim 2, wherein the cylinder-piston actuating mechanism comprises at least one piston chamber into which a hydraulic or pneumatic energy is introduced for tightening or releasing or retightening the tightening mechanism, wherein the tightening mechanism is tightened and retightened by at least one compression spring or tension spring, and wherein a piston of the cylinder-piston actuating mechanism has not moved against a piston chamber limitation in the locked state of the flexible arm so that there is a distance between the piston and the piston chamber limitation.

5. The surgical device according to claim 4, wherein the tightening and retightening of the tightening mechanism is effected by introducing the hydraulic or pneumatic energy, and the releasing of the tightening mechanism is effected exclusively by introducing the hydraulic or pneumatic energy.

6. The surgical device according to claim 2, wherein the traction cable is attached to an adapter section, and the adapter section is attached to the cylinder-piston actuating mechanism, and the adapter section and the cylinder-piston actuating mechanism are slidably arranged within the main body in the locked state of the flexible arm.

7. A surgical device for stabilizing tissue or for positioning organs or for positioning and holding surgical instruments and devices during a surgical intervention, comprising a main body and a flexible arm, which can be brought into different positions or locations and which can be locked in a desired positioning by a tightening mechanism, the tightening mechanism being tightened and released by an electric actuating motor, wherein, in a locked state of the flexible arm, the tightening mechanism has a retightening reserve, and the flexible arm can be automatically retightened in order to maintain a locked state using the retightening reserve, the surgical device comprising an electric control unit which, in the locked state of the flexible arm, detects a change in a tightening state of the tightening mechanism and controls an automatic retightening of the tightening mechanism based on the detected change by controlling the electric actuating motor.

8. The surgical device according to claim 7, wherein the electric actuating motor has a detection device that detects the change in the tightening state of the tightening mechanism, and automatically retightens the flexible arm based on a control by the electric control unit and based on the change detected by the detection device.

9. A surgical device for stabilizing tissue or for positioning organs or for positioning and holding surgical instruments and devices during a surgical intervention, comprising a main body and a flexible arm, which can be brought into different positions or locations and which can be locked in a desired positioning by a tightening mechanism, the tightening mechanism being tightened self-actingly by spring force and being released by an energy source, wherein, in a locked state of the flexible arm, the tightening mechanism has a retightening reserve, and the flexible arm can be automatically retightened, in order to maintain a locked state, using the retightening reserve, the retightening reserve being formed or released by a linearly movable stop which is linearly displaceable in the main body by the energy source.

10. The surgical device according to claim 9, wherein a detection device detecting a tightening state is provided, the tightening state being monitored by an electric control unit, and the energy source being provided for shifting the linearly moveable stop in a tightening direction, thereby releasing a spring travel reserve.

* * * * *